United States Patent [19]

Mann et al.

[11] 4,295,467
[45] Oct. 20, 1981

[54] ELECTROLYSIS APPARATUS WITH RETRACTABLE PROBE

[75] Inventors: Samuel J. Mann, Englewood; Michael Hrehovcik, Little Falls, both of N.J.

[73] Assignee: Inverness International Corp., River Edge, N.J.

[21] Appl. No.: 42,277

[22] Filed: May 24, 1979

[51] Int. Cl.³ .............................................. A61B 17/38
[52] U.S. Cl. .............................. 128/303.18; 128/800; 128/801
[58] Field of Search ...................... 128/303.13, 303.14, 128/303.17, 303.18, 303.19, 329 A, 735, 800, 801

[56] References Cited

U.S. PATENT DOCUMENTS

| | | | |
|---|---|---|---|
| 1,731,627 | 10/1929 | Johnson et al. | 128/303.18 |
| 2,417,530 | 3/1947 | Weiser | 128/303.13 |
| 2,447,127 | 8/1948 | Landaver | 128/800 |
| 2,894,512 | 7/1959 | Tapper | 128/303.18 |
| 3,054,405 | 9/1962 | Tapper | 128/303.18 |
| 4,043,342 | 8/1977 | Morrison, Jr. | 128/303.14 |

FOREIGN PATENT DOCUMENTS

| | | | |
|---|---|---|---|
| 2351748 | 4/1975 | Fed. Rep. of Germany | 128/303.18 |
| 2235669 | 1/1975 | France | 128/303.17 |

*Primary Examiner*—Lee S. Cohen
*Attorney, Agent, or Firm*—Blum, Kaplan, Friedman, Silberman & Beran

[57] ABSTRACT

An electrolysis apparatus for the removal of unwanted hair includes a probe which is retractable into a housing for protection of the probe. At least one of the conductive leads, which provide power to the device, is of a resilient material and is disposed for urging a slide within the apparatus toward a face thereof having an aperture, thereby facilitating movement of the slide by the operator of the apparatus for extruding and retracting the probe.

9 Claims, 10 Drawing Figures

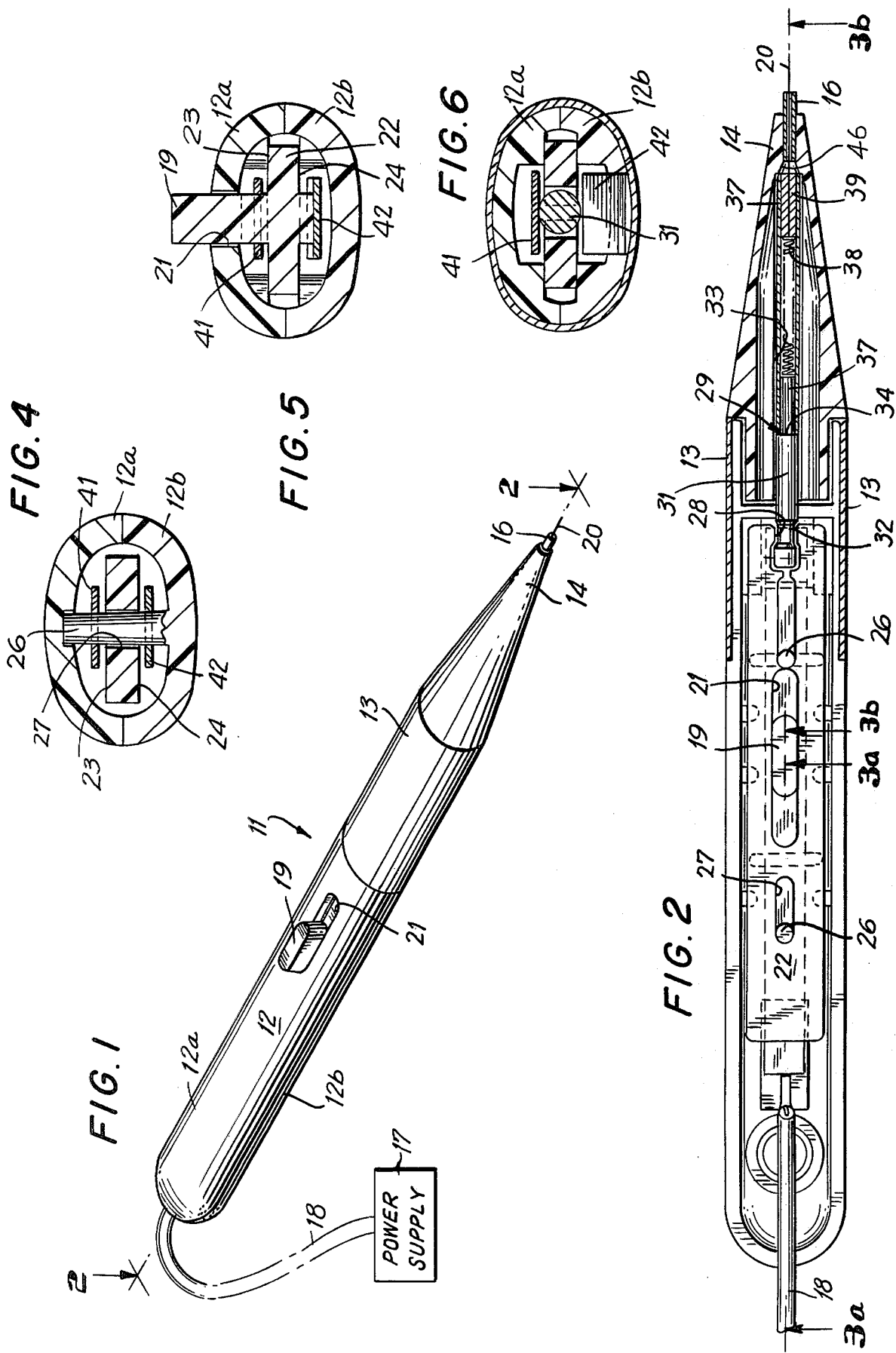

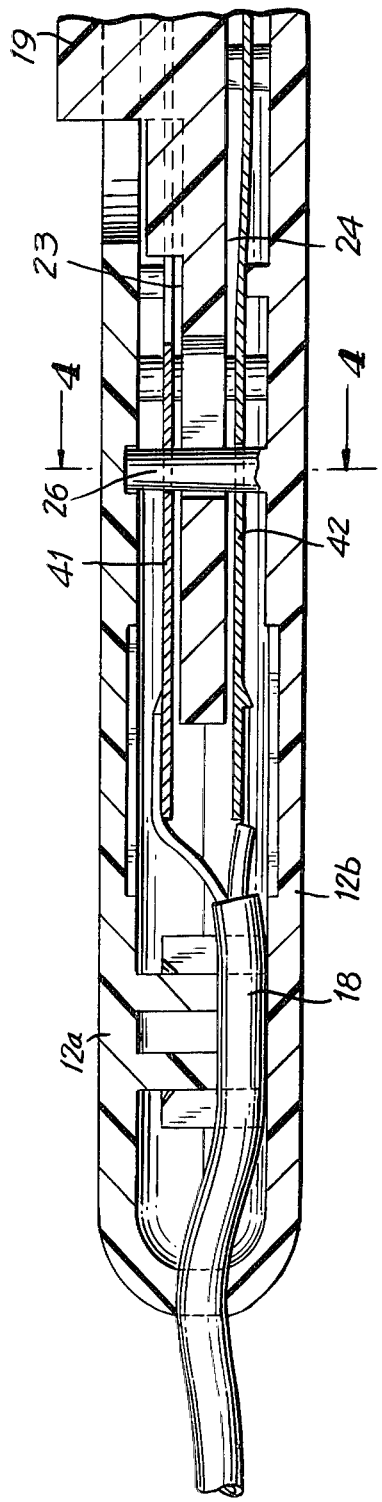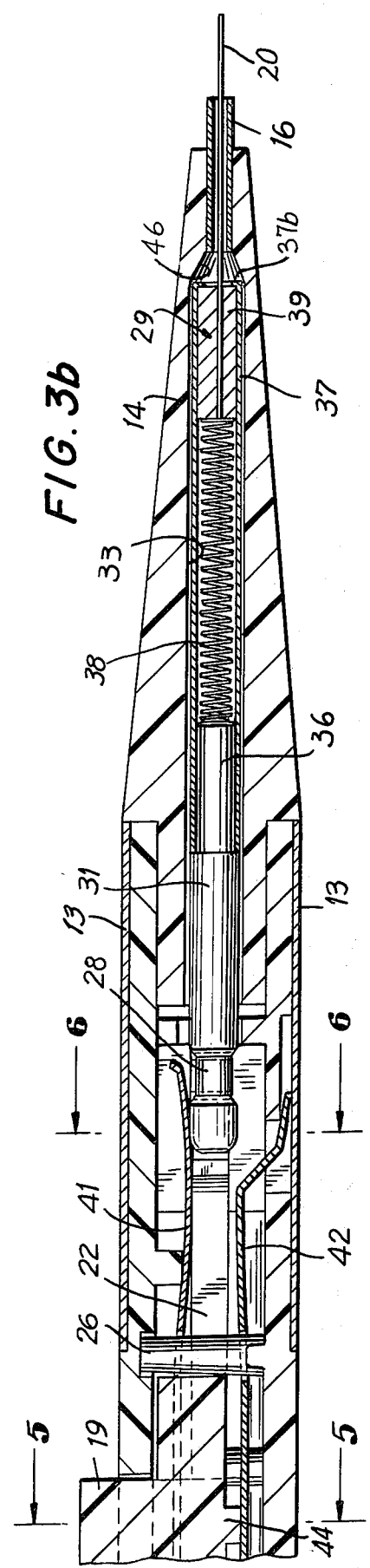

ELECTROLYSIS APPARATUS WITH RETRACTABLE PROBE

BACKGROUND OF THE INVENTION

This invention is directed to an electrolysis apparatus for the removal of unwanted hair and, in particular, to an electrolysis apparatus having a probe that is retractable into a housing for protecting the probe during non-use.

In the removal of unwanted hair by electrolysis, one type of apparatus includes a fine probe or stylet that is inserted into the pore from which such a hair is growing, the probe being inserted until it makes contact with or is proximate a papilla. Current is passed through the probe so as to electrolyze sodium chloride, thereby producing sodium hydroxide which destroys the papilla to prevent future growth of hair within the pore being treated and which makes it possible to extract the hair from the pore readily. A means of passing the current through a resilient probe and through the skin of the individual being treated is explained in U.S. Pat. No. 3,054,405 (Tapper). An improved electrolysis hair removal apparatus of this type is also explained in detail in co-pending application Ser. No. 964,866, filed Nov. 30, 1978, now U.S. Pat. No. 4,216,775, assigned to the same Assignee as this invention, said application being incorporated herein by reference as if fully presented.

Generally speaking, electrolytic reactions in aqueous solutions require a maximum voltage difference of no more than about 2 volts. However, due to the fact that skin resistance is involved, a somewhat larger voltage difference is required, a voltage of about 9 volts generally being found adequate. This voltage is low enough and the current involved is similarly low enough so that the fingers of the individual carrying out the treatment can be used as part of the electric circuit. For this purpose, it is convenient that the portion of the apparatus to be held by the operator thereof be conductive.

Since the probe must enter a pore in the skin, it must, of necessity, be of small diameter, and therefore fragile. As a result, the probe is subject to bending or breakage, especially when transported or otherwise out of use. Moreover, should the apparatus suffer a fall during use, the probe could readily be damaged. The present invention is concerned with protection of the probe as well as increasing the user's convenience in the use of the apparatus.

SUMMARY OF THE INVENTION

The apparatus of the present invention includes a housing and a retractable probe, extrusion of the probe from and retraction of the probe into the housing being effected by a slide within the housing. The slide is accessible through an aperture in a side face of the housing. The slide is preferably connected to the probe through a spring so that the probe is spring-biased outwardly during use thereof. The spring constant is such as to urge the probe with sufficient force so that it can enter a pore and reach the papilla but the force is not so great as to enable the probe to penetrate the skin of the user.

Preferably, a boss on the side of the slide extends through an aperture in the housing so that it can readily be manipulated from the exterior thereof. Further, it is preferred that at least one of the conductors providing current to the apparatus be of a resilient material and disposed for urging the slide toward the apertured face of the housing, thereby insuring ready accessibility of the slide for positioning the probe. The slide may have a boss thereon which protrudes through the aperture to facilitate extrusion and retraction of the probe.

The apparatus may be powered from an external source or by means of a battery contained within the housing.

Accordingly, an object of the present invention is an apparatus for the removal of hair by electrolysis, said apparatus having a retractable probe.

Another object of the present invention is an apparatus for the removal of hair by electrolysis wherein said probe is spring-biased with a force appropriate for inserting the probe into a pore, said force being inadequate for causing penetration of the skin by said probe.

A further object of the present invention is an apparatus for removal of hair by electrolysis wherein a slide within the apparatus for positioning the probe is urged toward an apertured face of the housing of the apparatus by one of the conductors of current to the probe.

Still other objects and advantages of the invention will in part be obvious and will in part be apparent from the specification.

The invention accordingly comprises the features of construction, combinations of elements and arrangements of parts which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings in which:

FIG. 1 is a perspective view of a retractable probe electrolysis apparatus constructed in accordance with a preferred embodiment of the present invention;

FIG. 2 is a sectional view taken along line 2—2 of FIG. 1;

FIG. 3a is a sectional view taken along line 3a—3a of FIG. 2;

FIG. 3b is a sectional view taken along line 3b—3b of FIG. 2;

FIG. 4 is a sectional view taken along line 4—4 of FIG. 3a;

FIG. 5 is a sectional view taken along line 5—5 of FIG. 3b;

FIG. 6 is a sectional view taken along line 6—6 of FIG. 3b;

DETAILED DESCRIPTION OF THE PREFERRED EMBODIMENTS

Figure 7:
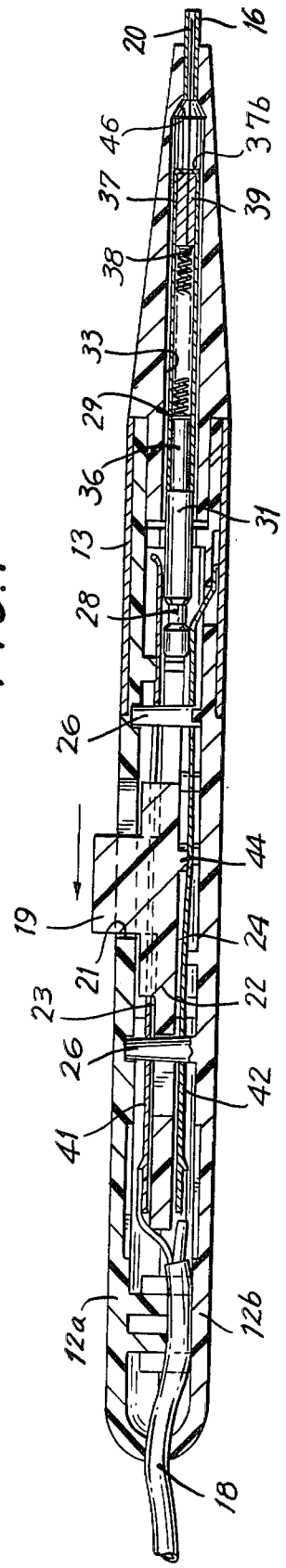
FIG. 7 is a longitudinal sectional view of the apparatus depicted in FIG. 1.

An electrolysis apparatus in accordance with the present invention is indicated generally in FIG. 1 by the reference numeral 11, said apparatus having a housing 12 including a conductive ferrule 13 and an end 14 in which is mounted hollow, cylindrical tip 16. In the embodiment of FIG. 1, power is supplied thereto from power supply 17 through twin flexible leads 18.

In the electrolysis apparatus of FIG. 1, the retractable probe, or stylet, is in retracted condition as indicated by the position of boss, or button 19, in slotted aperture 21. Considering the electrolysis apparatus, depicted in sectional view in FIG. 2, probe 20 is in a partially extruded position as is evident from the fact that button 19 is approximately at the center, longitudinally, of slotted aperture 21. Button 19 is attached to slide 22 which is mounted in housing 12 for being longitudinally displaced therein. Slide 22 is essentially rectangular in transverse cross-section, as can be seen from FIGS. 4, 5 and 6, having major upper and lower faces 23 and 24, respectively. The movement of slide 22 is guided by transverse pillars 26 which extend through slots 27 in slide 22.

Figure 8:
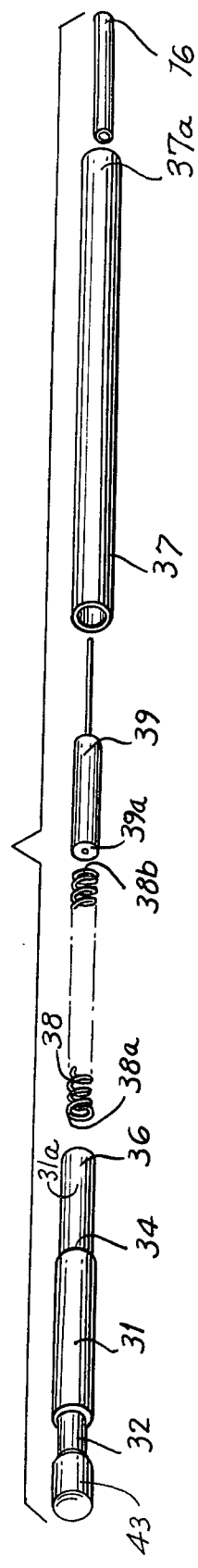
FIG. 8 is an exploded view, in perspective, of the probe depicted in FIG. 1, the cylindrical housing for same and the positioning means for extrusion and retraction of the probe.

Slide 22 has fingers 28 at one end thereof for linking said slide with the probe assembly, generally indicated as 29. As is best illustrated in FIG. 8, probe assembly 29 comprises a cylindrical rod 31 having a depression 32 proximate one end thereof for receiving fingers 28 of slide 22, the combination of fingers 28 and depression 32 linking slide 22 to rod 31. Probe assembly 39 is disposed in a hollow conduit 33 formed in housing 14. Rod 31 is adapted to slide in conduit 33 and includes a shoulder 34 against which is abutted extension rod 36 and interior cylinder 37 which sits within hollow conduit 33. Abutting the end 31a of extension rod 36 and joined thereto by welding, soldering or the like, is one end 38a of coil spring 38. The other end 38b of coil spring 38 is joined to one face 39a of a probe support conductive cylinder 39. Probe 20 is firmly seated in the probe support conductive cylinder 39. Rod 31, extension rod 36, spring 38, conductive cylinder 39 and probe 20 are all of electrically conductive material, suitable material being stainless steel, copper, nickel, brass, beryllium-copper and the like.

Electrical connection between the DC voltage supply 17 and conductive ferrule 13 and the probe assembly 29 is made through first resilient conductor 41 and second resilient conductive 42 which are firmly conductively bonded to flexible leads 18 as by well-known means, such as soldering or the like. As shown in FIG. 3a and FIG. 3b, the first resilient conductor 41 lies above upper face 23 of slide 22 and second conductor 42 lies below lower major face 24 of slide 22. This configuration is shown in FIGS. 4, 5 and 6 as well.

Accessibility to the interior of the electrolysis apparatus is provided by making housing 12 of an upper section 12a and a lower section 12b. To assemble the apparatus, end portion 14 is positioned against lower section 12b, the probe assembly 29 is inserted, second resilient conductor 42 is emplaced, slide 22 is fitted onto vertical pillars 26, first resilient conductor 41 is positioned over the slide so that it makes contact with head 43 of rod 31 and, finally, conductive ferrule 13 is snapped into place to hold the two segments of the housing together. Conveniently, conductive ferrule 13 may have a cut running the length thereof and may be curved to a diameter smaller than that of the housing so that it will act as a spring clip. Also, if desired, the two sections of the housing may be cemented together but it is preferable that it be possible to disassemble same to make maintenance possible.

As is evident, either first resilient conductor 41 or second resilient conductor 42 could be connected to rod 31 and the other to conductive ferrule 13, although as is illustrated in the drawings it is the second resilient conductor 42 which makes electrical contact with conductive ferrule 13. However, both resilient conductors are sufficiently resilient to insure good contact with conductive ferrule 13 and conductive rod 31. Further, second resilient conductor 42 is disposed so that it bears against the bottom of slide 22, thereby insuring that button 19 will protrude through aperture 21. In an exemplary embodiment, slide 22 includes a second boss 44 on the surface thereof against which second resilient conductor 42 bears. Accordingly, the second resilient conductor 42 has a double function, namely, making electrical contact with conductive ferrule 13 and resiliently biasing button 19 out through aperture 21 after the electrolysis apparatus is assembled.

Referring now to FIG. 7, the electrolysis apparatus with the probe 20 fully retracted into cylindrical tip 16 for protection thereby is depicted. Button 19 is fully retracted in slotted aperture 21 and slide 22 and probe assembly 29 and drawn into retracted position. Cylindrical rod 31, interior cylinder 37, spring 38 and cylinder 39 are also disposed in a retracted position. Spring 38 biases the probe support conductive cylinder 39 toward the end 37a of the interior cylinder, which includes a radially inwardly disposed lip 37b for preventing the probe support conductive cylinder 39 from being displaced out of the cylinder 37 by the biasing force of spring 38. When button 19 is moved to the right (FIG. 3b), probe 20 emerges from tip 16 after which end 37a of interior cylinder 37 makes contact with the diagonal shoulder 46, thereby preventing further outward movement of said interior cylinder. As probe 20 is moved into a pore and pressure is applied, cylinder 39 moves toward the retracted position against the urging of spring 38, thereby preventing the exertion of excessive pressure, whether the probe is in contact within the pore or positioned against the skin of the user.

The construction of the probe assembly is shown in more detail in FIG. 8. Preferably, extension rod 34 is so dimensioned that it fits tightly within interior cylinder 37 so the rod 31 and cylinder 37 move together. Also, probe 20 is firmly joined to metal cylinder 39, both mechanically and electrically. Hollow cylindrical tip 16 is held by friction in end 14 and, where appropriate, a suitable adhesive can be utilized to secure the cylindrical tip 16 in the end 14.

Figure 9:
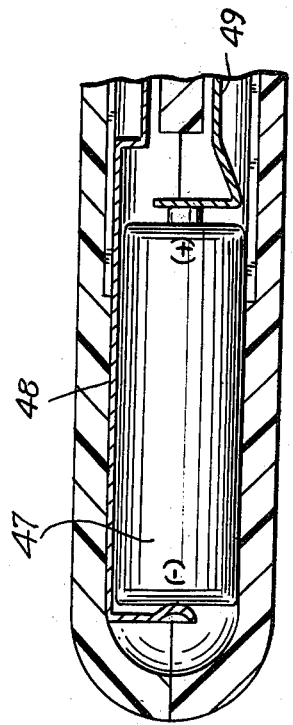
FIG. 9 is a sectional view of one end of an alternative embodiment of the apparatus depicted in FIG. 1 in which the power source for the probe is a battery contained in the housing.

Reference is now made to FIG. 9, wherein a retractable probe assembly, including a battery 47 for providing a convenient voltage of about 9 volts, is depicted. Power is transferred to a conductive ferrule 13 and to probe 16 in the same manner noted above. For example, resilient conductors 48 and 49 are otherwise identical with conductors 41 and 42, illustrated in FIGS. 3a and 3b. It is noted, however, that the resilient conductors 48 and 49 are configured to secure a battery in the probe assembly and to define a conductive circuit with the respective positive and negative terminals of the battery 47.

Thus, the instant invention is characterized by a conductive electrolysis probe that can be readily retracted into or extruded from a housing to thereby protect the probe during handling and storage of the electrolysis apparatus. Moreover, the probe remains resiliently biased when extruded from the housing to thereby insure the safety of the probe. Finally, the unique configuration of the resilient conductors and displacement mechanism, that permits the probe to be readily retracted and extruded, incorporates the resilient conductors required to couple the conductive ferrule and the probe to the appropriate terminals of the voltage supply needed to produce the voltage-current relationship necessary to effect the intended electrolysis operation.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

We claim:

1. An electrolysis apparatus comprising a housing including a probe end, said housing including a conductor means supported on said exterior thereof for defining a current path, an electrically conductive probe adapted to be coordinately displaced between an operative position wherein said probe extends from said probe end of said housing and an inoperative position wherein said probe is retracted into the probe end of said housing, positioning means associated with said housing and said probe for selectively displacing said probe between said operative position and said inoperative position, said positioning means including spring biasing means for biasing said probe against the papilla with a force normally sufficient for entry into a pore but normally insufficient to cause penetration of the skin when said probe is displaced in an operative position, first conductive means electrically connected with said conductor means and second conductive means electrically connected with said probe, said first and second conductive means being electrically connectable with a voltage source.

2. An electrolysis apparatus as claimed in claim 1, wherein said housing includes an aperture formed therein, said positioning means including a slide means extending through said aperture, said slide means being movable toward and away from said probe end for coordinately displacing said probe between said operative position and said inoperative position.

3. An electrolysis apparatus as claimed in claim 2, wherein said slide means includes a boss protruding through said aperture in said housing to the exterior of said housing.

4. An electrolysis apparatus as claimed in claim 2, wherein said positioning means includes conductive rod means having a first end joined with said slide means for movement therewith and having a second end, said spring biasing means connected with said second end of said rod means and with said probe for coordinately displacing said probe, said positioning means including conduit means for holding said rod means and spring biasing means coaxially positioned with respect to said probe and for receiving said probe when said probe is retracted into an inoperative position.

5. An electrolysis apparatus as claimed in claim 4, wherein said slide means is generally bar-shaped with rectangular cross-section and upper and lower major faces, said upper face being proximate said aperture, and one of said first and second conductive means is a resilient conductor for urging said slide means toward said aperture in said housing.

6. An electrolysis apparatus as claimed in claim 4, wherein said slide means includes fingers at one end thereof and said conductive rod means has a recess proximate said first end receiving said fingers and thereby connecting said rod means with said slide means for cooperating therewith in extruding and retracting said probe.

7. An electrolysis apparatus as claimed in claim 1, and including a first electrical lead means for coupling said conductor means through said first conductive means to said voltage source and a second electrical lead means for coupling said probe through said second conductive means to said voltage source.

8. An electrolysis apparatus as claimed in claim 1, and including a battery voltage source within said housing, said first and second conductive means positioning said battery in said housing and respectively coupling said probe and conductor means to said battery voltage source.

9. An electrolysis apparatus comprising a housing including a probe end, said housing having an aperture formed therein, said housing further including a conductor means supported on the exterior surface thereof for defining a current path, an electrically conductive probe adapted to be coordinately displaced between an operative position wherein said probe extends from said probe end of said housing and an inoperative position wherein said probe is retracted into the probe end of said housing, positioning means associated with said housing and said probe for selectively displacing said probe between said operative position and said inoperative position, said positioning means including a slide means extending through said aperture in said housing, said slide means being moveable toward and away from said probe end for coordinately displacing said probe between said operative position and said inoperative position, first conductive means electrically connected with said conductor means and second conductive means electrically connected with said probe, said first and second conductive means being electrically connectable with a voltage source and one of said first and second conductive means being a resilient conductor for urging said positioning means toward said aperture.

* * * * *